United States Patent [19]

Ho

[11] 4,309,352
[45] Jan. 5, 1982

[54] PROCESS FOR PRODUCING LACTONES FROM UNSATURATED CARBONYL COMPOUNDS

[75] Inventor: T. L. Ho, Jacksonville, Fla.

[73] Assignee: SCM Corporation, New York, N.Y.

[21] Appl. No.: 209,645

[22] Filed: Nov. 24, 1980

[51] Int. Cl.³ ................... C07D 307/32; C07D 309/30
[52] U.S. Cl. .............................. 260/343.5; 260/343.6
[58] Field of Search ........................... 260/343.5, 343.6

[56] References Cited

U.S. PATENT DOCUMENTS 3,527,769  9/1970  Matsui et al. .................... 260/343.5
3,565,915  2/1971  Matsui et al. .................... 260/343.5

OTHER PUBLICATIONS

Nebergall et al., College Chemistry with Qualitative Analysis, D. C. Heath & Co., 1968, p. 298.

Primary Examiner—Henry R. Jiles
Assistant Examiner—Jane T. Fan
Attorney, Agent, or Firm—Robert A. Sturges; Merton H. Douthitt

[57] ABSTRACT

A method for producing an alkyl substituted lactone including the steps of alkylating an unsaturated ketone with a $C_1$-$C_{12}$ alkyl organometallic reagent such as a Grignard reagent or an alkali metal alkyl, to form an unsaturated alcohol, and oxidatively cleaving the unsaturated alcohol to form the lactone, and recovering the lactone.

18 Claims, No Drawings

PROCESS FOR PRODUCING LACTONES FROM UNSATURATED CARBONYL COMPOUNDS

The present invention relates as indicated, to a method for producing aliphatic lactones. More particularly, the present invention relates to a method for the production of gamma, and delta-aliphatic lactones.

BACKGROUND OF THE INVENTION

Aliphatic lactones are particularly useful, especially in foodstuffs, because of their organoleptic properties. These materials have high flavor value due to their extremely low odor thresholds which average about 0.1 ppm.

While numerous methods are known for synthesizing lactones, especially from glycerides, higher molecular weight fatty acids and short chain functional group containing aliphatic compounds, many of the lactones are naturally occuring. The gamma-lactones occur mainly in plants, and the delta-lactones in animals.

An extensive literature survey relative to various lactones has been prepared by G. Ohloff and appears in Fortschritte d. Chem. Org. Naturstoffe, Volume 35, pages 431–527 (1978).

The present invention provides an improved method for making certain aliphatic lactones which are useful in small concentrations in food products as flavor and odor in parting materials. Moreover, these compounds have utility as intermediates in the preparation of still other odor and flavor imparting materials.

Lactones also have utility as solvents for polymers and copolymers of acrylonitrile. Reference may be had to the patent to Ham, U.S. Pat. No. 2,503,200 in this respect.

As indicated above, various methods are known for the preparation of aliphatic lactones. Reference may be had to U.S. Pat. No. 2,420,250 for one method of preparing gamma-valerolactones. According to this process, a 1,4-pentanediol is heated with a copper chromite catalyst under reflux conditions until the evolution of hydrogen ceases. The resulting reaction mixtures then distilled under reduced pressure to recover gamma-valerolactone.

According to U.S. Pat. Nos. 3,992,417 and 4,175,089, to Dessau et al, gamma-butyrolactones are formed by reacting an olefin with a compound containing a carboxylate group having at least one hydrogen atom on the alpha carbon atom in the presence of an ion of manganese, cerium or vanadium, the ion being in a valency state higher than its lowest valency state.

U.S. Pat. No. 2,569,064 discloses the preparation of gamma-lactones by heating a 2,2,4-trihalogenoalkanoic ester in the presence of catalyst such as zinc chloride, boron trifluoride, etc.

U.S. Pat. No. 2,968,568 discloses the preparation of butyrolactones by reacting bromoacetic acids and derivatives thereof with alpha olefins in the presence of a catalyst, preferably a free radical catalyst.

The present invention differs from the prior art in that the starting material is an unsaturated ketone which is alkylated by means of an organometallic compound, such as a Grignard reagent, to provide an alcohol containing an olefinic group. The resulting product is then oxidatively cleaved and cyclized to produce the lactone. The process is applicable to gamma and delta-lactones.

BRIEF STATEMENT OF THE INVENTION

Briefly stated, therefore, the present invention is in a process for producing an alkyl substituted lactone including the steps of reacting a mono-alkenyl carbonyl compounds containing at least five carbon atoms with a $C_1$–$C_{12}$ alkyl organometallic reagent or a metal hydride reagent to form an unsaturated alcohol. The alcohol is then oxidatively cleaved to form the corresponding $C_1$–$C_{12}$ alkyl substituted lactones. The lactone may then be recovered by any suitable means such as distillation at reduced pressures.

Stated in another way, the present invention comprises the steps of reacting a mono-alkenyl ketone or aldehyde having the general formula:

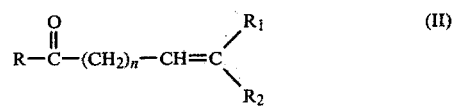

wherein R, $R_1$, and $R_2$ are independently selected from hydrogen and a $C_1$–$C_6$ alkyl group, and n is an integer selected from 2, and 3; with a hydride reagent or a $C_1$–$C_{12}$ alkyl organometallic compound having the general formula:

wherein M is an alkali metal, or magnesium halide, and $R_3$ is selected from hydrogen and $C_1$–$C_{11}$ alkyl groups. The reactions of these materials in a substantially one to one molar ratio results in the formation of an unsaturated alcohol having the general formula:

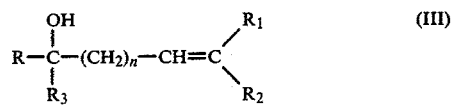

wherein R, $R_1$, $R_2$, $R_3$, and n have the meanings subscribed above. Thereafter, the unsaturated alcohols is oxidatively cleaved to form an alkyl substituted lactone having the general formula:

The resulting lactone (IV) is then recovered by usual means, for example, fractional distillation at reduced pressures. In the case where R in (II) above is an alkoxy group, the R in the resulting alcohol (III) and lactone (IV) becomes $R_3$ from (I). In other words the carbonyl center reacts twice with the $R_3M$ reagent (II).

DETAILED DESCRIPTION OF THE INVENTION AND SPECIFIC EXAMPLES

Equation 1 below is representative of the reactions occurring at each step in the present process. The unsaturated ketone aldehyde (2) is alkylated at the carbonyl group by an organometallic reagent such as a Grignard reagent

EQUATION 1

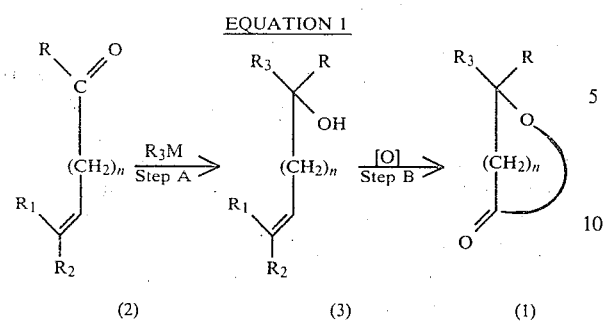

(2)           (3)           (1)

or an organolithium compound. Alkylation occurs at the carbonyl group which is converted to an unsaturated alcohol group (3). The unsaturated alcohol (3) is then oxidatively cleaved at the double bond to yield directly the alkyl substituted lactone (1). In a specific example, $R_3$ is $C_6H_{13}$ and n in the alcohol (3) is 2. Hence, the starting ketone is the readily available material 6-methyl-5-hepten-2-one. The lactone is gamma-methyl-gamma-decanolide. The yield in step A was 81% and in step B, 93.5%.

This novel procedure can be used to provide a large variety of lactone materials of the gamma- and delta-types (depending on the value of n in the foregoing formula (2). The R group of the organometallic reagent may be any alkyl or substituted alkyl group. Thus, R of the organo-metallic reagent may be alkyl such as, methyl, ethyl, propyl, isopropyl, n-butyl, sec-butyl, tert-butyl, n-amyl, and various other isomeric amyl radicals, n-hexyl and various other isomeric hexyl radicals, cyclohexyl, heptyl and various other heptyl radicals, methyl cyclohexyl, n-octyl, 2-ethyl hexyl, decyl, lauryl, dodecyl, etc.; benzyl, phenyl ethyl, etc. In the case of the Grignard reagents, these compounds have the general formula RMgX where R is the same as defined and exemplified above, and X is a halide, e.g., chlorine, bromine or iodine. Other organometallic reagents have the formula $(R)_mM$ where R is as defined and exemplified above, M is a metal selected from magnesium, alkali metal, e.g., sodium, lithium, and m is the valence of M. Particularly suitable $(R)_mM$ compounds are the alkyl lithium materials such as ethyllithium, n-butyllithium, n-hexyl lithium, n-dodecyl lithium, etc. These materials enable the alkylation group to be selected from a large variety of alkyl groups and substituted alkyl groups.

Specific examples of organometallic reagents useful herein include:
Grignard Reagents—RMgX
   methyl magnesium chloride
   methyl magnesium bromide
   methyl magnesium iodide
   ethyl magnesium chloride
   ethyl magnesium iodide
   ethyl magnesium bromide
   i-propyl magnesium chloride
   n-propyl magnesium bromide
   n-butyl magnesium bromide
   i-butyl magnesium bromide
   n-pentyl magnesium chloride
   n-hexyl magnesium bromide
   cyclohexyl magnesium chloride
   cyclohexyl magnesium bromide
   methyl cyclohexyl magnesium bromide
   benzyl magnesium bromide
   phenyl ethyl magnesium bromide, etc.
Metal Alkyls—$R_mM$
   methyl lithium
   ethyl lithium
   sec-butyl lithium
   ethyl sodium
   t-amyl lithium
   n-hexyl lithium
   cyclohexyl lithium
   benzyl lithium, etc.

The starting unsaturated ketones or aldehydes (II) have the general formula:

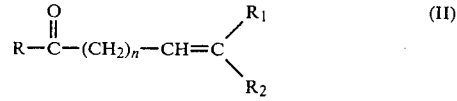

wherein R is hydrogen or a $C_1$–$C_6$ alkyl group, $R_1$ and $R_2$ are independently selected from hydrogen and a $C_1$–$C_6$ alkyl group and n is 1, 2, or 3. Examples of alkyl groups suitable for use as R, $R_1$, and $R_2$ include methyl (preferred), ethyl, propyl, isopropyl, n-butyl, sec.-butyl, i-butyl; n-pentyl methyl substituted butyls, n-hexyl, cyclohexyl, etc. Specific examples of unsaturated ketones and aldehydes useful in the process of this invention include, therefore,
   4-pentenal
   4-hexenal
   4-chloro-4-pentenal
   5-hexenal
   5-methyl-4-hexenal
   5-phenyl-4-pentenal
   5-hexen-2-one
   5-chloro-5-hexen-2-one
   6-hepten-2-one
   6-hepten-3-one
   6-methyl-5-hexen-2-one
   6-methyl-5-hepten-2-one
   6-phenyl-5-hexen-2-one In general, the organometallic reagent and the unsaturated carbonyl compound (II) are reacted in at least a 1:1 mole ratio. Preferably, the organometallic reagent is utilized in excess, e.g., from about 1:1 up to about 1.5:1 mole ratio. The reaction medium may be any suitable low boiling inert solvent, e.g., the same medium in which the organometallic reagent is prepared, or a different solvent, e.g., diethyl ether, dioxane, tetrahydrofuran, methyl-n-butyl ether, etc. or mixed solvents (ether-hydrocarbons). The reaction is conveniently carried out at reflux under ambient pressure. At higher geographic elevations, pressure to ~760 Torr. may be applied, or a higher boiling solvent utilized. A satisfactory yield is obtained generally in less than 10 hours. After reaction, the reaction mass is cooled and desirably quenched with water. It should be noted that the reflux temperatures are relatively low, that is less than about 150° C. to as low as about 30° C. Any remaining unreacted organometallic may be decomposed in situ, e.g., with aqueous ammonium chloride, and separated. The supernatant solvent layer is evaporated to recover the solvent and the residue vacuum distilled to recover the resulting unsaturated tertiary alcohol.

The oxidative cleavage reaction necessary for lactone formation is conveniently carried out at a temperature sufficiently low to enable control of the oxidation reaction. The temperature will depend, therefore, on the oxidative power of the agent employed. Ozone is a powerful cleavage agent, albeit convenient to handle in the reaction. Suitable oxidizing agents also include potassium permanganate, ruthenium tetroxide.

To carry out the cleavage reaction, a solution of the unsaturated alcohol in acetone, or other suitable low boiling solvent, is formed and the solution cooled by any suitable means, e.g., a dry ice/isopropanol bath. Ozone is passed through the solution until it is detected in the exit gas by iodide test. Excess ozone in the reaction mass is removed, and the ozonide is further heated with Jones' reagent while the temperature is maintained at −78° C. The reagent turns orange at the end point. The solvent is then evaporated from the reaction mixture and water added to the residue. Methylene chloride may be used to extract the lactone. Evaporation of the solvent yields the final lactone which is purified by distillation under vacuum. Oxidizing systems other than Jones' reagent, such as acidic or alkaline hydrogen peroxide may be used; especially when the unsaturated alcohol containing secondary hydroxyl group.

The lactones produced in accordance herewith are used in known manners to provide flavors and aromas to foodstuffs. Gamma-ethyl-gamma valerolactone is readily produced in high yield from dihydrolinalool.

The present invention will be better understood from the following specific examples, it being understood that these examples are for the purpose of illustrating the invention and are not intended as limiting the invention to the scope thereof.

EXAMPLE I

5-Methyl-1-undecen-5-ol

5-Hexen-2-one (11.8 g. 0.12 mol) was added dropwise to the Grignard reagent formed from magnesium (3.6 g., 0.15 mol) and 1-bromohexane (24.8 g., 0.15 mol) in ether (150 ml). After the addition, the reaction mixture was refluxed for 2 hours, and cooled. Upon quenching with aqueous ammonium chloride, layers were separated. The ether solution was evaporated and distilled to give 5-methyl-1-undecen-5-ol (18.1 g., 82% yield; b.p. 90°–95°/0.5 torr).

EXAMPLE II

4-methyl-4-decanolide from 5-methyl-1-undecen-5-ol

A solution of 5-methyl-1-undecen-5-ol (9.2 g., 0.05 mol) in acetone (100 ml) was cooled in a dry-ice-isopropanol bath while a stream of ozone was bubbling through it. When reaction was complete, excess ozone was expelled with oxygen and the reaction mixture was treated with Jones' reagent until an orange color persisted. Acetone was removed by evaporation and the residue was distributed between water and methylene chloride. The organic solution was separated, washed with water, and evaporated. The residue was distilled to give 4-methyl-4-decanolide (8.2 g., 89% yield; b.p. 108°–113°/0.5 torr).

EXAMPLE III

1-Undecen-5-ol 4-pentenal (8.4 g., 0.1 mol) was added dropwise to the Grignard reagent from magnesium turnings (2.88 g., 0.12 mol) and 1-bromohexane (19.8 g., 0.12 mol) in ether (120 ml). The reaction mixture was then refluxed for 2 hours cooled, and quenched with ammonium chloride solution. After layers were separated, ether solution was evaporated and the residue distilled to give 1-undecen-5-ol (15.0 g., 88% yield, b.p. 93°–96°/1.2 torr).

EXAMPLE IV

4-Decanolide 1-undecen-5-ol (8.5 g., 0.005 mol) dissolved in methanol (100 mL) was ozonized while being cooled in a dry ice-isopropanol bath. Upon completion of ozonolysis, excess ozone was expelled with a stream of oxygen, the ozonide was then treated with 50% $H_2O_2$ (10 ml) and 10% sodium hydroxide (40 ml) at room temperature for 20 hour. Acidification and extraction with methylene chloride yielded a product which was distilled to give 4-decanolide (5.5 g., 65% yield; b.p. 140°–145°/10 torr).

What is claimed is:

1. The method of making an alkyl substituted lactone which comprises the steps of reacting a hydride reagent or a $C_1$–$C_{12}$ alkyl organometallic compound having the formula:

$$R_3M \qquad (I)$$

wherein $R_3$ is selected from hydrogen and $C_1$–$C_{11}$ alkyl or substituted alkyl groups, M is an alkali metal or magnesium halide, with a mono-alkenyl carbonyl having the formula:

$$\underset{\text{}}{\overset{O}{\underset{\|}{R-C}}-(CH_2)_n-CH=C\begin{matrix}R_1\\ \diagdown \\ R_2\end{matrix}} \qquad (II)$$

wherein R is a hydrogen, $C_1$–$C_6$ alkyl group or alkoxy group and $R_1$, and $R_2$ are independently selected from hydrogen and a $C_1$–$C_6$ alkyl group, and n is an integer selected from 2 and 3, to form an unsaturated alcohol having the formula:

$$\underset{\underset{OH}{|}}{\overset{R_3}{\underset{|}{R-C}}-(CH_2)_n-CH=C\begin{matrix}R_1\\ \diagdown \\ R_2\end{matrix}} \qquad (III)$$

wherein R, $R_1$, and $R_3$ and n have the meanings ascribed above, the reactants (I) and (II) being present in a molar ratio of at least about 1:1, oxidatively cleaving (III) to form an alkyl substituted lactone having the formula:

$$\underset{\underset{\longleftarrow O \longrightarrow}{}}{\overset{R_3}{\underset{|}{R-C}}-(CH_2)_n-\overset{O}{\underset{\|}{C}}} \qquad (IV)$$

wherein R, $R_3$ and n are as described above, and recovering said lactone (IV).

2. The method of making an alkyl substituted lactone which comprises the steps of reacting a $C_1$–$C_{12}$ alkyl organometallic compound having the formula:

$$R_3M \qquad (I)$$

wherein $R_3$ is selected from hydrogen and $C_1$–$C_{11}$ alkyl or substituted alkyl groups and M is an alkali metal or magnesium halide with a mono-alkenyl carbonyl compound having the formula:

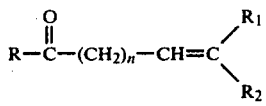

wherein R is hydrogen, a $C_1$–$C_6$ alkyl group or alkoxy group and $R_1$, and $R_2$ are independently selected from hydrogen and a $C_1$–$C_6$ alkyl group, and n is an integer selected from 2 and 3, to form an unsaturated alcohol having the formula:

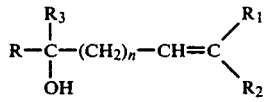

wherein R, $R_1$, $R_2$, and $R_3$ and n having the meanings ascribed above, the reactants (I) and (II) being present in a molar ratio of at least 1:1, oxidatively cleaving (III) to form an alkyl substituted lactone having the formula:

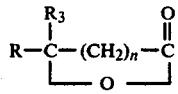

wherein R, $R_3$ and n are as described above and recovering said lactone (IV).

3. The method of claim 1 wherein the organometallic reagent is a Grignard reagent.

4. The method of claim 1 wherein the organometallic compound has the general formula:

$R_3$—Mg—X wherein X is a halide.

5. The method of claim 4 wherein the halide is bromine.

6. The method of claim 4 wherein the organometallic compound is n-hexyl magnesium bromide.

7. The method of claim 1 wherein the organometallic reagent is an alkyl alkali metal.

8. The method of claim 7 wherein the alkyl alkali metal is an alkyl lithium.

9. The method of claim 8 wherein the alkyl lithium is n-hexyl lithium.

10. The method of claim 1 wherein the oxidative cleavage is effected with ozone.

11. The method of claim 1 wherein the oxidative cleavage is effected with ozone.

12. The method of claim 10 wherein the oxidative cleavage is carried out at a sub-zero temperature.

13. The method of claim 11 wherein the oxidative cleavage is carried out at a sub-zero temperature.

14. The method as defined in claim 1 wherein the ketone is 6-methyl-5-heptene-2-one.

15. The method as defined in claim 14 wherein the organometallic compound is n-hexyl-magnesium bromide.

16. The method as defined in claim 15 wherein the oxidative cleavage is effected with ozone.

17. The method as defined in claim 16 wherein the oxidative cleavage is carried out at a sub-zero temperature.

18. The method of making an alkyl substituted lactone which comprises the steps of reacting a mono-alkenyl carbonyl compound containing at least 5 carbon atoms with a hydride reagent or a $C_1$–$C_{12}$ alkyl organometallic reagent in a molar ratio of at least about 1:1 to form an unsaturated alcohol, oxidatively cleaving said unsaturated alcohol to form the corresponding alkyl substituted lactone, and recovering said lactone.

* * * * *

UNITED STATES PATENT AND TRADEMARK OFFICE
CERTIFICATE OF CORRECTION

PATENT NO. : 4,309,352
DATED : 01/05/82
INVENTOR(S) : Tse-Lok Ho

It is certified that error appears in the above—identified patent and that said Letters Patent are hereby corrected as shown below:

IN THE CLAIMS:

Claims 3, 7, 10 and 14, line 1 of each, change the numeral "1" to ---18---.

Signed and Sealed this

Eleventh Day of May 1982

[SEAL]

Attest:

GERALD J. MOSSINGHOFF

Attesting Officer     Commissioner of Patents and Trademarks